United States Patent
Howard et al.

(10) Patent No.: US 9,248,096 B2
(45) Date of Patent: Feb. 2, 2016

(54) AMPHIPATHIC LIPID-BASED SUSTAINED RELEASE COMPOSITIONS

(71) Applicant: Pegasus Laboratories, Inc., Kansas City, MO (US)

(72) Inventors: Scott A. Howard, Pace, FL (US); Troy Purvis, Brandon, MS (US)

(73) Assignee: PEGASUS LABORATORIES, INC., Kansas City, MO (US)

( * ) Notice: Subject to any disclaimer, the term of this patent is extended or adjusted under 35 U.S.C. 154(b) by 0 days.

(21) Appl. No.: 13/690,974

(22) Filed: Nov. 30, 2012

(65) Prior Publication Data

US 2013/0142876 A1    Jun. 6, 2013

Related U.S. Application Data

(60) Provisional application No. 61/566,279, filed on Dec. 2, 2011.

(51) Int. Cl.
| | |
|---|---|
| A61K 9/00 | (2006.01) |
| A61K 9/20 | (2006.01) |
| A61K 31/09 | (2006.01) |
| A61K 31/137 | (2006.01) |
| A61K 31/485 | (2006.01) |

(52) U.S. Cl.
CPC ............ A61K 9/0056 (2013.01); A61K 9/2013 (2013.01); A61K 31/09 (2013.01); A61K 31/137 (2013.01); A61K 31/485 (2013.01)

(58) Field of Classification Search
None
See application file for complete search history.

(56) References Cited

U.S. PATENT DOCUMENTS

| | | | |
|---|---|---|---|
| 5,993,850 A | 11/1999 | Sankaram et al. | |
| 6,077,534 A * | 6/2000 | Tobin et al. | 424/462 |
| 2005/0008701 A1 | 1/2005 | Sriwongjanva et al. | |
| 2006/0134208 A1 * | 6/2006 | Villa et al. | 424/468 |
| 2007/0141096 A1 | 6/2007 | Van Lengerich | |
| 2007/0298101 A1 * | 12/2007 | Wiackowski et al. | 424/465 |
| 2008/0220079 A1 * | 9/2008 | Chen et al. | 424/490 |
| 2010/0062988 A1 | 3/2010 | Chen et al. | |
| 2010/0166810 A1 | 7/2010 | Habboushe | |

FOREIGN PATENT DOCUMENTS

WO    WO-2010-136193    * 12/2010

OTHER PUBLICATIONS

The International Search Report and the Written Opinion dated Mar. 27, 2013 in the related PCT/US2012/067361 filed on Nov. 30, 2012.

* cited by examiner

*Primary Examiner* — Frederick Krass
*Assistant Examiner* — Celeste A. Roney
(74) *Attorney, Agent, or Firm* — Hovey Williams LLP; Gregory J. Skoch (57) ABSTRACT

Chewable sustained release compositions and their methods of production are provided. The sustained release compositions contain amphipathic lipids, which are used to encapsulate various drugs and active ingredients.

24 Claims, 5 Drawing Sheets

AMPHIPATHIC LIPID-BASED SUSTAINED RELEASE COMPOSITIONS

RELATED APPLICATION

The present application claims the benefit of U.S. Provisional Patent Application No. 61/566,279, filed Dec. 2, 2011, the entirety of which is incorporated by reference herein.

BACKGROUND OF THE INVENTION

1. Field of the Invention

The present invention is directed to chewable sustained release compositions and to methods of preparing and using such compositions.

2. Description of the Related Art

Sustained release compositions have been developed to provide a slow and sustained release of a drug or active ingredient into a subject over an extended period of time. Thus, sustained release compositions mitigate the necessity for multiple daily dosings of certain drugs and other active ingredients. However, most existing sustained release compositions are not suitable as chewable formulations. In fact, chewing most sustained release compositions will inhibit their ability to slowly release the drug or active ingredient over an extended period of time and will result in an uncontrolled burst of the drug or active ingredient. Furthermore, most sustained release compositions have an unacceptable taste when chewed, which decreases the willingness of many patients to accept such tablets.

Chewable tablets of sustained release compositions have been increasingly utilized in various pharmaceutical and veterinary markets due to their ability to sustain constant drug release over an extended time period and maintain taste-masking properties even after being chewed into smaller fragments. For instance, chewable sustained release tablets have developed a niche in veterinary medicine because many of the treated animals tend to chew any medicine given orally. Chewable sustained release tablets are also increasingly being used in human medicine for patients who have difficulties in swallowing or taking intact medications.

Recently, wax-based agents have been incorporated into chewable sustained release compositions in an attempt to provide the desired sustained release and taste-masking properties. For instance, U.S. Patent Application No. 2010/0062988 discloses chewable sustained release compositions produced by using dispersions of the vegetable protein zein coupled with wax-like agents and a spheronizing agent to encapsulate drugs and other active ingredients. The zein/wax matrix is able to produce a chewable sustained release composition that can add a degree of taste-masking to bitter tasting drugs. Similarly, U.S. Patent Application Publication No. 2008/0220079 utilizes wax-like agents in conjunction with a spherizonizing agent to produce a chewable sustained release composition that can encapsulate drugs and other active ingredients. However, the chewable sustained release compositions in both of these publications require that the compositions be heated to a temperature exceeding the melting points of the wax-like agent in order to effectively encapsulate the drug or active ingredient. Unfortunately, this additional heating step can increase the costs of producing these chewable sustained release compositions and potentially damage the encapsulated drug or active ingredient.

Accordingly, there is a need for a chewable sustained release composition, and a process for making such, that is capable of maintaining a sustained release of a drug or active ingredient over an extended time period and that exhibits certain taste-masking properties.

SUMMARY OF INVENTION

In one embodiment of the present invention, a sustained release composition is provided. The sustained release composition comprises (a) between about 0.5% to about 80% by weight of one or more active ingredients; (b) between about 0.5% to about 80% by weight of one or more amphipathic lipids; and (c) between about 5% to about 90% by weight of at least one bulking or spheronizing agent. The active ingredients are encapsulated within a matrix comprising the amphipathic lipids and the bulking or spheronizing agent. The composition exhibits an in vitro dissolution rate of the active ingredients, as measured by a USP Dissolution Apparatus II, of about 10% to 50% after about 2 hours, about 25% to 90% after about 4 hours, more than about 60% after about 12 hours, and more than about 75% after about 16 hours.

In another embodiment of the present invention, a sustained release composition is provided. The sustained release composition comprises (a) between about 0.5% to about 80% by weight of one or more active ingredients; (b) between about 0.5% to about 80% by weight of one or more amphipathic lipids selected from the group consisting of phospholipids and lecithins; and (c) between about 5% to about 80% by weight of at least one bulking or spheronizing agent. The active ingredients are encapsulated within a matrix comprising the amphipathic lipids and the bulking or spheronizing agent. The composition exhibits an in vitro dissolution rate of the active ingredients, as measured by a USP Dissolution Apparatus II, of about 10% to 90% after about 2 hours, about 20% to 90% after about 4 hours, more than about 60% after about 12 hours, and more than about 70% after about 16 hours.

In yet another embodiment of the present invention, a process to produce a sustained release composition is provided. The process comprises the steps of: (a) combining one or more active ingredients and one or more lipids in a solvent to produce an active-containing solution or suspension; (b) mixing the active-containing solution or suspension with at least one spheronizing or bulking agent to produce a mixture; and (c) forming the mixture into tablets. The tablets exhibit an in vitro dissolution rate of the active ingredients, as measured by a USP Dissolution Apparatus II, of about 10% to 90% after about 2 hours, about 20% to 90% after about 4 hours, more than about 60% after about 12 hours, and more than about 70% after about 16 hours. In addition, steps (a)-(c) are performed at temperatures that do not exceed the melting points of the lipids.

DETAILED DESCRIPTION

The present disclosure is directed to chewable sustained release compositions that comprise at least one amphipathic lipid. An "amphipathic lipid," as used herein, pertains to any molecule that is lipophilic and has at least one region that is polar or ionic (i.e., hydrophilic). The sustained release compositions of the present disclosure can comprise, consist essentially of, or consist of: (i) at least one active ingredient, (ii) at least one amphipathic lipid, and (iii) at least one bulking and/or spheronizing agent. Furthermore, the sustained released composition of the present disclosure can take the form of tablets or multiparticulates. In certain embodiments, the sustained release compositions provided herein are capable of maintaining the sustained release of active ingredients subsequent to chewing or being fragmented into smaller pieces. In other embodiments, the compositions of the present disclosure have minimal initial burst of active ingredients to enable the making of taste-masking formulations.

Unless indicated otherwise, any weight percentage is the weight of the listed component relative to the total weight of a composition, to the total weight of a tablet, or to the total weight of a multiparticulate.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used in the present disclosure, the term "about" refers to any value in the range of 90% to 110% of the specified value.

Amphipathic Lipids

The sustained release composition of the present disclosure comprises one or more amphipathic lipids. In certain embodiments, the amphipathic lipids can comprise at least about 0.5, 1, 2, 3, 4, 5, 6, 7, 8, 9, 10, 15, 20, 25, 30, 35, 40, 45, or 50 weight percent of the composition, tablet, or multiparticulate. Additionally or alternatively, the amphipathic lipids can comprise no more than about 80, 75, 70, 65, 60, 55, 50, 45, 40, 35, 30, 25, 20, 15, 10, or 5 weight percent of the composition, tablet, or multiparticulate.

In one embodiment, the amphipathic lipids can include any lipid that exhibits both hydrophilic and lipophilic properties. In certain embodiments, the amphipathic lipids are selected from the group consisting of phospholipids, lecithins, steroids, sphingolipids, ceramides, and glycolipids. In a more particular embodiment, the amphipathic lipids are selected from the group consisting of phospholipids and lecithins. In one embodiment, the amphipathic lipids do not include lipids formed from hydrophobic polymers and/or hydrophilic polymers.

Phospholipids are amphipathic lipids that generally contain lipophilic hydrocarbon tails and a hydrophilic head comprising a phosphate group. Due to this hydrophilic head, phospholipids can be readily soluble or dispersable in various organic solvents. Lecithin is generally an unrefined mixture of phospholipids that contains a non-defined ratio of phosphatidylcholine. The ratio of phosphatidylcholine in the lecithin depends on the source of the lecithin.

In one embodiment, the phospholipids comprise phosphatidylcholine, phosphatidylethanol, phosphatidylserine, or mixtures thereof. In another embodiment, the phospholipids comprise at least about 5, 10, 15, or 20 and/or not more than 99, 95, or 90 weight percent of phosphatidylcholine. Exemplary phospholipids include, for example, PHOSPHOLIPON 90H and PHOSPHOLIPON 20 from LIPOID (Newark, N.J.). Exemplary lecithins include, for example, ULTRALEC from ARCHER DANIELS MIDLAND (Decatur, Ill.) and lecithin from BULKFOODS.COM (Toledo, Ohio).

Steroids are amphipathic lipids that generally contain a base structure of at least four cycloalkane rings that are joined together. Various functional groups can be attached to this four ring core in order to impart hydrophilic properties onto the steroid. Exemplary steroids include, for example, cholesterol.

The amphipathic lipids can include, for example, lipids that are suspended, dispersed, or dissolved in an aqueous, hydroalcoholic, or organic solvent. In one embodiment, the amphipathic lipids can be suspended, dispersed, or dissolved in a solvent selected from the group consisting of methanol, ethanol, n-propanol, isopropanol, t-butanol, ethyl acetate, acetone, and mixtures thereof. In an alternative embodiment, the amphipathic lipids do not include solutions of polymers in organic solvents.

In certain embodiments, the amphipathic lipids are not exposed to any temperatures that exceed their melting points during the production of the sustained release compositions. For example, during production of the sustained release compositions, the amphipathic lipids may not be subjected to temperatures exceeding 120° C., 110° C., 100° C., 90° C., 80° C., 70° C., 60° C., 50° C., 40° C., 35° C., or 30° C. Unlike conventional wax-based lipids, amphipathic lipids do not need to be melted in any degree in order to effectively encapsulate the active ingredients. The absence of a heating step can reduce production costs and minimize potential degradation to the active ingredients during production.

It is theorized that the mechanism involved in this disclosure is based on the formation of a solid matrix of the active ingredient by the amphipathic lipids. The amphipathic lipids "seal" the active ingredients by embedding the active ingredient in the matrix. For clarification, the amphipathic lipids of this disclosure are not used as a coating.

Active Ingredients

As used in the present disclosure, the term "active ingredient" includes any active pharmaceutical ingredient(s) and nutraceutical ingredient(s). The active ingredients in the composition may be any active ingredients (i.e., a compound or a composition) with beneficial pharmaceutical, therapeutic, nutritional, or cosmetic effects. The active ingredients can comprise at least about 0.5, 1, 2, 3, 4, 5, 6, 7, 8, 9, 10, 15, 20, 25, 30, 35, 40, 45, 50, 55, or 60 weight percent of the composition, tablet, or multiparticulate. Additionally or alternatively, the active ingredients can comprise no more than about 95, 90, 85, 80, 75, 70, 65, 60, 55, 50, 45, 40, 35, 30, 25, 20, 15, or 10 weight percent of the composition, tablet, or multiparticulate.

In certain embodiments, the active ingredient is phenylpropanolamine ("PPA") or its pharmaceutically acceptable salt (e.g., phenylpropanolamine hydrochloride). PPA has been used as a decongestant and an appetite suppressant in humans. In veterinary medicine, it is also used to control urinary incontinence in dogs.

In certain embodiments, the active ingredient may be one or more analgesics or pharmaceutically acceptable salts thereof, such as acetaminophen, a centrally acting analgesic agent, opiate, narcotic, nonsteroidal anti-inflammatory drugs ("NSAID"), and/or salicylate. Exemplary NSAIDs include, for example, aspirin, carprofen, deracoxib, etodolac, firocoxib, celecoxib, diclofenac, diflunisal, flurbiprofen, ibuprofen, indomethacin, ketoprofen, kietorolac, mefenamic acid, meloxicam, naproxen, phenylbutazone, piroxicam, rofecoxib, sulindac, tepoxalin, valdecoxib, and/or vedaprofen.

In certain embodiments, the active ingredient may be one or more medications for treating respiratory congestion, allergy symptoms, nasal discharge, or tussis. These include, for example, bromopheniramine, chlorpheniramine, dextromethorphan, diphenhydramine, ephedrine, guaifenesin, PPA, pseudoephedrine, and/or acceptable salts thereof.

In certain embodiments, the active ingredient may be an anti-epileptic, anti-seizure, anti-convulsant, or GABA-ergics. These include, for example, barbiturates, benzodiazepines, carbamates, carbamazepines, gabapentin, oxazoladinediones, phenyloin, potassium bromide, pregabalin, pyrrolidines, succinimides, sulfonamides, triazines, topiramate, valproamines, zonisamide, and/or acceptable salts thereof.

In certain embodiments, the active ingredient is a dietary supplement or nutraceutical, such as vitamins, multi-vitamins (i.e., a mixture of multiple vitamins, such as a mixture of two or more fat-soluble vitamins, a mixture of two or more water-soluble vitamins, and a mixture of one or more fat-soluble vitamins and one or more water-soluble vitamins), minerals, herbs or other botanicals, amino acids, proteins (e.g., milk protein concentrates), antioxidants (e.g., grape seed extract and milk thistle), anti-inflammatory agents (e.g., bromelain), carotenoids (e.g., lycopene and lutein), flavonoids (e.g., quercetin and rutin), prebiotics (e.g., arabinogalactan and fructooligosaccharides), and/or weight loss agents (e.g., *garcinia cambogia*).

In certain embodiments, the active ingredient is one or more anti-infective or anti-microbial agents or pharmaceutically acceptable salts thereof including, for example, β-lactam antibiotics (e.g., amoxicillin, ampicillin, and ceftiofur), lincosamides, clindamycin, aminoglycosides, cephalosporins, macrolides, ketolides, penicillins, quinolones, sulfonamides, tetracyclines (e.g., doxycycline), cycloserine, vancomycin, linezolid, oxazolidinone, pyrimethamine, atovaquone, tigecycline, glycylcyclines, anthelmintics, antifungals, antimalarial agents, antiprotozoal agents, leprostatics, antituberculosis agents, and/or anti-parasitics. In other embodiments, the anti-infective agent is azithromycin, clarithromycin, roxithromycin, erythromycin, telithromycin, ciprofloxacin, a combination of amoxicillin and clavulanate potassium, and/or a pharmaceutically acceptable salt thereof.

In certain embodiments, the active ingredient is a thyroid or a thyroid modulating agent, including levothyroxine sodium useful for treating hypothyroidism and methimazole useful for treating hyperthyroidism.

In certain embodiments, the active ingredient is a behavior modifying drug, such as anti-anxiety agents and antidepressants. Exemplary behavior modifying drugs include, for example, buspirone hydrochloride, fluoxetine hydrochloride, paroxetine, amitriptyline hydrochloride, clomipramine hydrochloride, doxepin, and imipramine hydrochloride.

In certain embodiments, the active ingredient is an anti-diabetic agent. Exemplary anti-diabetic agents include, for example, glipizide, metformin, acarbose, and glibenclamide.

In certain embodiments, the active ingredient is a phosphate binding compound. Exemplary compounds include, for example, sevelamer hydrochloride, aluminum carbonate, and aluminum hydroxide.

In certain embodiments, the active ingredient is one or more antiviral agents or a pharmaceutically acceptable salt thereof, such as, for example, abacavir, acyclovir, ganciclovir, lamivudine, nelfinavir, ritonavir, valacyclovir, and zidovudine.

In certain embodiments, the active ingredient is an antacid such as, for example, sodium antacids (e.g., trisodium phosphate), calcium antacids (e.g., calcium carbonate), aluminum antacids (e.g., aluminum hydroxide), magnesium antacids (e.g., magnesium hydroxide), and combinations thereof.

In certain embodiments, the active ingredient is one or more insect growth regulators ("IGR") or pharmaceutically acceptable salts thereof such as, for example, methoprene, kinoprene, hydroprene, diflubenzuron, and/or pyriproxyfen.

In certain embodiments, the active ingredient is one or more antioxidants or pharmaceutically acceptable salts thereof such as, for example, ascorbic acid, bromelain, grapeseed extract, milk thistle, rose hip, alpha lipoic acid, beta carotene, lycopene, lutein, and/or alpha tocopherol.

In certain embodiments, the active ingredient is a high dose active ingredient. An active ingredient of "high dose" refers to an active ingredient that is orally administered at a daily dose of about or greater than 1 mg/kg body weight to an adult human patient or an adult non-human subject. In one embodiment, the active ingredient has a daily dose about or greater than 2, 3, 4, 5, 6, 7, 8, 9, 10, 20, 30, 40, or 50 mg/kg body weight for an adult human or an adult non-human subject. In another embodiment, the active ingredient has a daily dose about or greater than 100, 200, 250, 300, 350, 400, 450, 500, 600, 700, 800, 900, or 1000 mg for an adult human or an adult non-human subject. In yet another embodiment, the active ingredients are those that must be given at about 200 mg, 300 mg, 400 mg, 500 mg, 600 mg, 700 mg, 800 mg, 900 mg, or 1 g per dose in a twice-a-day, once-a-day, or once-per-treatment regimen.

Exemplary active ingredients of high dose include, for example, guaifenesin (100 mg/dose or more), acyclovir (200 mg/dose), acetaminophen (300 mg/dose), metformin (500 mg/dose), gabapentin (100-800 mg/dose), glucosamine, glucosamine sulfate, and glucosamine HCl (500 mg/dose).

In certain embodiments, the active ingredient has a short half-life. An active ingredient of "short half-life" refers to an active ingredient that has a half-life about or less than 12 hours. In other embodiments, the active ingredient of the present disclosure has a half-life of about or less than about 11, 10, 9, 8, 7, 6, 5, 4, 3, or 2 hours in a human or non-human subject. In general, an active ingredient of a short half-life is required to be taken more than twice a day in its immediate release forms to maintain the efficacious blood concentration level through the day.

In certain embodiments, the active ingredient may be insoluble, slightly soluble, sparingly soluble, soluble, freely soluble, or very soluble in water.

In certain embodiments, the composition may further comprise a second active ingredient. In one embodiment, the other active ingredient may have the same or similar pharmacological effect as the first active ingredient. In another embodiment, the second active ingredient may have a pharmacological effect different from the first active ingredient.

Secondary Sustained Release Agent

In certain embodiments, a secondary sustained release agent can be added to the composition in order to supplement and reinforce the amphipathic lipids. In such an embodiment, the secondary sustained release agent comprises at least about 0.5, 1, 2, 3, 4, 5, 6, 7, 8, 9, 10, 15, 20, 25, 30, 35, 40, 45, or 50 weight percent of the composition, tablet, or multiparticulate. Additionally or alternatively, the secondary sustained release agent can comprise no more than about 80, 75, 70, 65, 60, 55, 50, 45, 40, 35, 30, 25, 20, 15, 10, or 5 weight percent of the composition, tablet, or multiparticulate.

In one embodiment, the secondary sustained release agent is different from the amphipathic lipids. The secondary sustained release agent can comprise, for example, esters of a fatty alcohol and a saturated and/or unsaturated fatty acid, saturated and unsaturated fatty acid glycerides (mono-, di-, or triglycerides), hydrogenated fats, hydrogenated vegetable oils, cholesterol, hydrocarbons, waxes, hydrophobic polymers having a hydrocarbon backbone, hydrophilic polymers having a hydrocarbon backbone, or a combination thereof.

In one embodiment, the secondary sustained release agent comprises a wax, such as animal and insect waxes (e.g., beeswax, Chinese wax, shellac wax, spermaceti wax, and lanolin wax), vegetable waxes (e.g., bayberry wax, candelilla wax, carnauba wax, castor wax, esparto wax, Japan wax, jojoba oil, ouricury wax, and rice bran wax), mineral waxes (e.g., ceresin waxes, montan wax extracted from lignite and brown coal, ozocerite, and peat waxes), petroleum waxes (e.g., paraffin wax and microcrystalline wax), and/or synthetic waxes (e.g., polyethylene waxes, chemically modified waxes, substituted amide waxes, and polymerized alpha-olefins).

In another embodiment, the secondary sustained release agent comprises vegetable wax, candelilla wax, carnauba wax, castor wax, esparto wax, Japan wax, jojoba oil, ouricury wax, and/or rice bran wax.

In yet another embodiment, the secondary sustained release agent comprises hydrogenated vegetable oils such as, for example, hydrogenated cottonseed oil, partially hydrogenated cottonseed oil, hydrogenated soybean oil, partially hydrogenated soybean oil, and stearyl alcohol.

Bulking or Spheronizing Agents

The sustained release compositions of the present disclosure also comprise one or more bulking or spheronizing agents. The bulking or spheronizing agents can comprise at least about 5, 10, 15, 20, 25, 30, 40, 45, or 50 weight percent of the composition, tablet, or multiparticulate. Additionally or alternatively, the bulking or spheronizing agent can comprise no more than about 95, 90, 85, 80, 75, 70, 65, 60, 55, or 50 weight percent of the composition, tablet, or multiparticulate.

A "bulking agent," as used herein, refers to an agent that enhances the ability of the sustained release composition to form into a cohesive plastic mass that can subsequently be granulated or extruded and compressed into tablets.

A "spheronizing agent," as used herein, refers to an agent that enhances the ability of the sustained release composition to form into a cohesive plastic mass that may be subsequently spheronized to produce spherical pellets or fragmented to form non-spherical pellets.

In one embodiment, the bulking or spheronizing agent is selected from a group consisting of microcrystalline cellulose, starch, sodium carboxymethylcellulose, pregelatinized starch, dicalcium phosphate, powdered sugar, calcium phosphate, calcium sulfate, lactose, mannitol, kaolin, sodium chloride, sorbitol, and combinations thereof. In certain embodiments, the bulking or spheronizing agent is microcrystalline cellulose. In other embodiments, the bulking or spheronizing agent is a combination of microcrystalline cellulose and dicalcium phosphate.

Sustained Release

The sustained release composition of the present disclosure provides sustained release of the active ingredient. The term "sustained release," as used herein, refers to a release of an active ingredient that occurs more slowly relative to an immediate release dosage form. The term may be used interchangeably with "slow-release," "controlled release," "modified release," or "extended release." The sustained release property of a composition is typically measured by an in vitro dissolution method and confirmed by an in vivo blood concentration-time profile (i.e., a pharmacokinetic profile).

The term "immediate release dosage forms" refers to release forms wherein at least 75% of the active ingredient is released or dissolved within about one-half hour after in vivo administration or in an in vitro dissolution assay as known in the art or tested using a USP Dissolution Apparatus II.

In certain embodiments, the sustained release composition releases the active ingredient in a nearly linear fashion for at least about 2, 3, 4, 5, 6, 7, 8, 9, 10, 11, 12, 14, or 16 hours. An active ingredient is released in a "nearly linear" fashion for a specified period of time if the release rate of the agent does not change more than 20% during each hour within the specified period of time.

In certain embodiments, the sustained release composition has an in vitro dissolution rate, as measured by a USP Dissolution Apparatus II, of at least about 5%, 10%, 15%, 20%, 25%, or 30% of the active ingredient released after 2 hours, at least about 10%, 15%, 20%, 25%, 30%, 35%, or 40% of the active ingredient released after 4 hours, at least about 20%, 25%, 30%, 35%, 40%, 45%, or 50% of the active ingredient released after 6 hours, at least about 25%, 30%, 35%, 40%, 45%, or 50% of the active ingredient released after 8 hours, at least about 30%, 35%, 40%, 45%, 50%, or 55% of the active ingredient released after 10 hours, at least about 35%, 40%, 45%, 50%, 55%, 60%, 65%, or 70% of the active ingredient released after 12 hours, and/or at least about 40%, 45%, 50%, 55%, 60%, 65%, 70%, 75%, or 80% of the active ingredient released after 16 hours.

In certain embodiments, the sustained release composition has an in vitro dissolution rate, as measured by a USP Dissolution Apparatus II, of no more than about 10%, 20%, 30%, 40%, 50%, 60%, 70%, 80%, or 90% of the active ingredient released after 2 hours, no more than about 20%, 30%, 40%, 50%, 60%, 70%, 80%, or 90% of the active ingredient released after 4 hours, no more than about 30%, 40%, 50%, 60%, 70%, 80%, or 90% of the active ingredient released after 6 hours, no more than about 40%, 50%, 60%, 70%, 80%, or 90% of the active ingredient released after 8 hours, no more than about 50%, 60%, 70%, 80%, or 90% of the active ingredient released after 10 hours, no more than about 60%, 70%, 80%, or 90% of the active ingredient released after 12 hours, and/or no more than about 70%, 80%, or 90% of the active ingredient released after 16 hours.

The term "initial burst" refers to uncontrolled or quick release of the active ingredient (e.g., greater than 10% of the drug load) from a dosage form immediately following an exposure to an aqueous medium (such as saliva or gastric fluid). A burst is undesired as it defeats the purpose of a sustained release and/or taste-masking for a chewable composition.

In certain embodiments, the sustained release composition can have minimal initial burst of no more than about 10%, 9%, 8%, 7%, 6%, 5%, 4%, 3%, 2% or 1% during the first 1 to 5 minutes as measured in an in vitro dissolution assay by a USP Dissolution Apparatus II. Such a feature allows the making of taste-masking formulations, especially desirable for active ingredients with unpleasant tastes (e.g., phenylpropanolamine, ibuprofen, acetaminophen, and certain vitamins).

In certain embodiments, the sustained release compositions are chewable. "Chewable," as used herein, refers to the ability of a tablet or multiparticulate composition to maintain its sustained release property and taste-masking property if fragmented into a plurality of smaller pieces.

In certain embodiments, when the tablets or multiparticulates are broken into a plurality of fragments, the fragmented composition can maintain an in vitro dissolution rate of the active ingredient, as measured by a USP Dissolution Apparatus II, of no more than about 90%, 80%, 70%, 60%, 50%, 40%, 30%, or 20% of the active ingredient released after 2, 3, 4, 5, 6, 7, 8, 9, 10, 11, or 12 hours.

In certain embodiments, the average in vitro dissolution rate of the sustained release composition in tablet or multiparticulate forms, as measured by a USP Dissolution Apparatus II, does not increase by more than about 100%, 90%, 80%, 70%, 60%, 50%, 40%, 30%, 20% or 10% during the first 2, 4, 6, 8, 10, or 12 hours when the tablets or pellets are fragmented.

In certain embodiments, the sustained release composition, when administered orally to a patient in need of the equivalent daily dose of an immediate release formulation, provides a plasma concentration of its active ingredient at or above its minimum effective concentration for a period of time at least about the same as, or about 1.5, 2, 3, 4, or 5 times of, that of the immediate release formulation administered at a daily standard dose (i.e., the daily dose according to the official product description for the formulation or the dose approved by a regulatory authority for the formulation).

Multiparticulates

In certain embodiments, the sustained release composition is in the form of multiparticulates, which are discrete particles that make up a multiple-unit dosage form. Multiparticulates include, for example, pellets (e.g., spherical or non-spherical pellets) and granules.

The term "pellets" refers to small particles with approximately uniform shapes and sizes produced by an extrusion process. A "small particle" refers to a particle of which diameter, length, height, and width is at most 10 mm (e.g., at most 2, 3, 4, 5, 6, 7, 8, or 9 mm).

In certain embodiments, the composition of the present disclosure is in the form of spherical pellets. The term "spherical pellet" refers to beads, beadlets, spherical particles, spheroids, or the like that are of round or about round in shape and are generally made by an extrusion and spheronization process.

Additional Ingredients and Coatings

Optionally, the sustained release composition may comprise one or more excipients, including binders, antioxidants, colorants, lubricants, glidants, and flavoring agents. In one embodiment, the excipients can comprise at least about 0.1, 1, 5, 10, or 15 and/or no more than about 50, 40, 25, 20, 15, or 10 by weight of the composition, tablet, or multiparticulate.

Suitable binders include water-soluble hydroxyalkyl celluloses such as povidone, polyvinylpyrrolidone, xanthan gum, cellulose gums (e.g., hydroxypropyl cellulose, hydroxypropyl methylcellulose ("HPMC"), and sodium carboxymethylcellulose sodium ("CMC")), gelatin, starch, and/or water-insoluble polymers (e.g., pre-gelatinized starch, acrylic polymers or copolymers, or alkyl celluloses such as ethyl cellulose).

Suitable antioxidants include butylated hydroxyanisole ("BHA"), butylated hydroxytoluene ("BHT"), vitamin E, and/or ascorbyl palmitate.

Suitable colorants may be selected from any FD&C pigments or dyes.

Suitable lubricants include talc, stearic acid, vegetable oil, calcium stearate, zinc stearate, and/or magnesium stearate.

Suitable glidants include talc, silicon dioxide, and cornstarch.

Other excipients that may be incorporated into the sustained release compositions include preservatives or any other excipient commonly used in the pharmaceutical industry.

In certain embodiments, the composition of the present disclosure is optionally coated for additional drug release control, appearance, moisture protection, taste, or flavor improvement.

The term "sustained release barrier coating" refers to a coating on the tablets or multiparticulates that substantially slows the release of the active ingredient. More specifically, the presence of a sustained release barrier coating reduces the in vitro dissolution rate of the active ingredient within the first two hours by at least about 50%.

Suitable sustained release coating materials include water-insoluble waxes and polymers such as hydrogenated vegetable oil (e.g., hydrogenated cottonseed oil), polymethacrylates, and/or water-insoluble celluloses (e.g., ethylcellulose).

Exemplary Embodiments

Unless otherwise provided, the exemplary formulations described in this section may comprise any active ingredient, especially one or more of those specifically described above, any amphipathic lipid, any secondary sustained release agent, and any bulking or spheronizing agent. In addition, such exemplary formulations can be in tablet or multi-particulate forms and provide sustained release of the active ingredient.

In certain embodiments, the composition of the present disclosure in a tablet or multiparticulate form comprises, consists essentially of, or consists of: (a) from about 1% to about 70% by weight of an active ingredient; (b) from 1% to 30% by weight of one or more amphipathic lipids; (c) from about 10% to about 80% by weight of secondary sustained release agent, and (d) from about 5% to about 70% by weight of a bulking or spheronizing agent.

In certain embodiments, the composition of the present disclosure in a tablet or multiparticulate form comprises, consists essentially of, or consists of: (a) from about 0.5% to about 20% by weight of an active ingredient; (b) from about 0.5% to about 40% by weight of one or more amphipathic lipids; and (c) from about 10% to about 60% by weight of a one or more bulking or spheronizing agents.

In certain embodiments, the composition of the present disclosure in tablet or multiparticulate forms comprises, consists essentially of, or consists of: (a) from about 3% to about 25% by weight of an active ingredient; (b) from 1% to 15% by weight of one or more amphipathic lipids; (c) from about 5% to about 55% by weight of a secondary sustained release agent, and (d) from about 15% to about 45% by weight of a bulking or spheronizing agent.

In certain embodiments, the composition of the present disclosure in a tablet or multiparticulate form comprises, consists essentially of, or consists of: (a) from about 1% to about 80% by weight of an active ingredient; (b) from 1% to 30% by weight of phospholipids from an alcoholic dispersion; (c) from about 1% to about 70% by weight of hydrogenated vegetable oil, stearic acid, or vegetable wax, and (d) from about 5% to about 50% by weight of microcrystalline cellulose, pregelatinized starch, or a mixture thereof.

In certain embodiments, the composition of the present disclosure in a tablet or multiparticulate form comprises, consists essentially of, or consists of: (a) from about 3% to about 25% by weight of an active ingredient; (b) from 1% to 15% by weight of phospholipids from an alcoholic dispersion; (c) from about 1% to about 25% by weight of hydrogenated vegetable oil, stearic acid, or vegetable wax, and (d) from about 15% to about 45% by weight of microcrystalline cellulose, ethylcellulose, dicalcium phosphate or a mixture thereof.

In certain embodiments, the composition of the present disclosure in a tablet or multiparticulate form comprises, consists essentially of, or consists of: (a) from about 0.5% to about 20% by weight of phenylpropanolamine hydrochloride; (b) from 0.5% to 10% by weight of phospholipids from an alcoholic dispersion; (c) from about 10% to about 40% by weight of microcrystalline cellulose, and (d) from about 5% to about 25% by weight of dicalcium phosphate.

In certain embodiments, the composition of the present disclosure in a tablet or multiparticulate form comprises, consists essentially of, or consists of: (a) from about 1% to about 10% by weight of phenylpropanolamine hydrochloride; (b) from 5% to 25% by weight of phospholipids from an alcoholic dispersion; (c) from about 40% to about 65% by weight of hydrogenated vegetable oil or vegetable oil (e.g., hydrogenated cottonseed oil, stearic acid, and carnauba wax), (d) from about 15% to about 35% by weight of microcrystalline cellulose, and (e) from about 10% to about 20% by weight of dicalcium phosphate.

In certain embodiments, the composition of the present disclosure in a tablet or multiparticulate form comprises, consists essentially of, or consists of: (a) from about 1% to about 50% by weight of multi-vitamins and minerals, (b) from about 1% to about 25% by weight of phospholipids from an alcoholic dispersion, (c) from about 1% to about 20% by weight of hydrogenated vegetable oil or vegetable wax (e.g., hydrogenated cottonseed oil, stearic acid, or carnauba wax), and (d) from about 10% to about 50% by weight of microcrystalline cellulose.

In certain embodiments, the composition of the present disclosure in a tablet or multiparticulate form comprises, consists essentially of, or consists of: (a) from about 5% to about 30% by weight of a water-soluble drug or salt thereof, (b) from about 1% to about 25% by weight of phospholipids from an alcoholic dispersion, (c) from about 5% to about 50% by weight of hydrogenated vegetable oil or vegetable wax (e.g., hydrogenated cottonseed oil, stearic acid, or carnauba wax), and (d) from about 15% to about 60% by weight of microcrystalline cellulose.

In certain embodiments, the composition of the present disclosure in a tablet or multiparticulate form comprises, consists essentially of, or consists of: (a) about 8% or 9% by weight of phenylpropanolamine hydrochloride; (b) about 8.5% by weight of phospholipids from an alcoholic dispersion; (c) about 10% by weight of hydrogenated vegetable oil, stearic acid, or vegetable wax (e.g., hydrogenated cottonseed oil and carnauba wax), (d) about 24% by weight of microcrystalline cellulose, and (e) about 14% by weight of dicalcium phosphate.

In certain embodiments, the composition of the present disclosure in a tablet or multiparticulate form comprises, consists essentially of, or consists of: (a) about 8.25% by weight of phenylpropanolamine hydrochloride; (b) about 16.5% by weight of phospholipids from an alcoholic dispersion; (c) about 48% by weight of hydrogenated vegetable oil, stearic acid, or vegetable wax (e.g., hydrogenated cottonseed oil and carnauba wax), (d) about 24% by weight of microcrystalline cellulose, and (e) about 14% by weight of dicalcium phosphate.

In certain embodiments, the composition of the present disclosure in a tablet or multiparticulate form comprises, consists essentially of, or consists of: (a) about 10% by weight of phenylpropanolamine hydrochloride; (b) about 8.5% by weight of phospholipids from an alcoholic dispersion; (c) about 1 to about 10% by weight of hydrogenated vegetable oil, stearic acid, or vegetable wax (e.g., hydrogenated cottonseed oil and carnauba wax), (d) about 27% by weight of microcrystalline cellulose, and (e) about 24% by weight of dicalcium phosphate.

In certain embodiments, the composition of the present disclosure in a tablet or multiparticulate form comprises, consists essentially of, or consists of: (a) about 8.25% by weight of guaifenesin; (b) about 8.25% by weight of phospholipids from an alcoholic dispersion; (c) about 1% by weight of hydrogenated vegetable oil, stearic acid, or vegetable wax (e.g., hydrogenated cottonseed oil and carnauba wax), (d) about 25% by weight of microcrystalline cellulose, and (e) about 33% by weight of dicalcium phosphate.

In certain embodiments, the composition of the present disclosure in a tablet or multiparticulate form comprises, consists essentially of, or consists of: (a) about 0.9% by weight of dextromethorphan HBr; (b) about 8.25% by weight of phospholipids from an alcoholic dispersion; (c) about 1% by weight of hydrogenated vegetable oil, stearic acid, or vegetable wax (e.g., hydrogenated cottonseed oil and carnauba wax), (d) about 25% by weight of microcrystalline cellulose, and (e) about 40% by weight of dicalcium phosphate.

Dosage Forms

In another aspect, oral dosage forms that comprise the compositions disclosed herein are provided. The term "oral dosage form" refers to a device that collectively delivers, by oral ingestion, the desired amount of an active ingredient, to achieve a desired dose of the active ingredient. Typically, the oral dosage form is a powder for oral suspension, a unit dose packet or sachet, a tablet, or a capsule.

In certain embodiments, the pellets of the present disclosure may be mixed with a vehicle and packaged in a container such as a screw cap bottle. Prior to dosing, the mixture is added with water or another liquid and shaken to form an "oral suspension." In this oral suspension, the pellets containing the active ingredient may be (a) completely suspended in the vehicle, or (b) partially suspended in the vehicle and partially in solution with the vehicle.

In certain embodiments, the multiparticulate composition of the present disclosure may be mixed with or placed on feed to allow the animal patient to eat voluntarily.

The term "vehicle" refers to a mixture that facilitates the suspension of pellets and improves the taste of an oral suspension. A vehicle useful in this invention may contain suspending agents, anti-caking agents, fillers, sweeteners, flavorants, colorants, and/or lubricants.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and/or titanium dioxide.

Examples of anti-caking agents or fillers include colloidal silicon oxide and lactose.

In certain embodiments, the dosage form may be packaged in a bottle, packet, pouch, sachet, or capsule.

In certain embodiments, the dosage form comprises the active ingredient at a dose of at least about 10, 20, 50, 100, 200, 250, 300, 400, 500, 600, 700, 750, 800, or 900 mg, or about 1, 2, 3, 4, 5, 6, 7, 8, 9, or 10 gram per dose.

In certain embodiments, the dosage form is for single dose use. "Single dose," as used herein, refers to administering only one dose of an active ingredient in the full course of therapy.

In certain embodiments, the dosage form, upon oral administration to a patient in need thereof, provides a plasma concentration of the active agent in the patient at or above its minimum effective concentration for at least about 2, 4, 6, 8, 10, 12, 14, 16, 18, 20, 24, 36, 48, 72, 96, 120, 144, or 168 hours.

In certain embodiments, the dosage form, upon oral administration to a patient in need thereof, provides a plasma concentration of the active agent in the patient at or above its minimum effective concentration for a period of time that is at least about 2, 3, 4, or 5 times of that of an immediate release formulation administered at a standard dose.

Methods of Producing the Sustained Release Composition

In another aspect, the present disclosure provides a method for making the compositions and dosage forms described herein.

In certain embodiments, the present disclosure provides a method for making the sustained release composition that comprises: (a) combining one or more active ingredients and one or more amphipathic lipids in a solvent to produce an active-containing solution or suspension; (b) mixing the active-containing solution or suspension with at least one spheronizing or bulking agent to produce a mixture; and (c) forming the mixture into tablets. In such an embodiment, steps (a)-(c) are performed at temperatures that do not exceed the melting point of the amphipathic lipids. The solvent can be selected from the group consisting of methanol, ethanol, n-propanol, isopropanol, t-butanol, ethyl acetate, acetone, and mixtures thereof.

In another embodiment, the method comprises: (a) combining one or more active ingredients and one or more amphipathic lipids in a solvent to produce an active-containing solution or suspension; (b) mixing the active-containing solution or suspension with at least one spheronizing or bulking agent to produce a mixture; (c) granulating or extruding the mixture of step (b) to obtain wet granules or extrudates, (d) drying the granules or extrudates to produce a dry granule or extrudate, and (e) sizing the dry granules or fragmenting the dry extrudates to form pellets. In such an embodiment, steps (a)-(e) are performed at temperatures that do not exceed the melting point of the amphipathic lipids. In another embodiment, steps (a)-(e) are performed at temperatures that do not exceed 120° C., 110° C., 100° C., 80° C., 60° C., 50° C., 40° C., 35° C., or 30° C. In yet another embodiment, at least 75, 80, 85, 90, 95, 99, or 99.9 percent of the active ingredient added in step (a) remains present in the extrudates, granules, or pellets in steps (d) or (e).

As used herein, the term "granules" refers to small particles without approximately uniform shapes and sizes formed by the process in the present disclosure. Granules generally are less uniform in size or shape than pellets.

In certain embodiments, the dry granules or pellets are further filled into capsules.

In certain embodiments, the dry granules or pellets are further coated with a coating composition provided herein.

In certain embodiments, the dry granules or pellets are further mixed with other tabletting ingredients and compressed into tablets. In other embodiments, the tablets are further coated with a coating composition provided herein.

The drying step is primarily used to remove water, hydroalcoholic, or organic solvent from the mixture and to cause the granules/extrudates/pellets to sufficiently harden. A lower temperature (e.g., no more than about 40° C., 35° C., or 30° C.) is usually sufficient for the drying purpose and is preferred for the stability of the active ingredient. In a preferred embodiment, the drying step does not occur at temperatures that exceed the melting points of the amphipathic lipids. For instance, the drying step does not exceed temperatures of 120° C., 110° C., 100° C., 80° C., 60° C., 50° C., 40° C., 35° C., or 30° C.

The drying time may vary from 10 minutes to several hours or longer depending upon the batch size, efficiency of the dryer used, and the drying temperature. The drying stage will continue until a substantial portion of the water, hydroalcoholic, or organic solvent has been removed from the granules or extrudates. As used herein, the term "dry," as used in conjunction with the granules, extrudates, and pellets, refers to granules, extrudates, or pellets having a residual solvent content of less than 10 weight percent. In other embodiments, the drying step can continue until the granules, extrudates, or pellets contain a residual solvent content of no more than 7, 5, or 3 weight percent.

In certain embodiments, the drying step may be performed in a lyophilizer, fluid bed process, convection oven, or microwave oven.

In certain embodiments, the method of the present disclosure does not utilize a heating step that uses temperatures exceeding the melting points of the amphipathic lipids. In such an embodiment, the active ingredients exhibit little or no degradation during the production method provided herein.

In certain embodiments, the dry granules, pellets, extrudates, or tablets produced via the above extrusion process are further coated with a coating composition. Such a coating composition may comprise amphipathic lipids, a secondary sustained release agent, a flavorant, a colorant, or a combination thereof.

Methods of Using Compositions

In one aspect, the present disclosure provides methods for using the sustained release compositions and dosage forms described herein for treating or preventing diseases or disorders. The diseases or disorders include, for example, incontinence, congestion, hypothyroidism, hyperthyroidism, anxiety, depression and other behavioral disorders, pain, inflammation, infection, diabetes, hyperphosphataemia, chronic diseases, and dietary deficiencies. As previously mentioned, the sustained release composition described herein can be used to treat diseases or disorders in human or non-human patients.

This invention can be further illustrated by the following examples of embodiments thereof, although it will be understood that these examples are included merely for the purposes of illustration and are not intended to limit the scope of the invention unless otherwise specifically indicated.

ENABLING EXAMPLES

The following examples are provided by way of illustration, and not by way of limitation.

Example 1

Chewable sustained release tablets containing PPA were prepared by first mixing phospholipids (PHOSPHOLIPON 90, "PL90H") with a PPA dissolved in ethanol at about 30° C.

to about 40° C. to produce a dispersion. Using a low-shear mixer, microcrystalline cellulose, liver blend, and dicalcium phosphate were mixed with the dispersion to produce a wet-mass material. Extrudates (i.e., wet granules) were produced by passing the wet-mass material through a 16-mesh screen. The granules were dried at ambient temperature over night until the moisture level was not more than 5% by weight. The dried granules were then further fragmented by forcing them through a 10-mesh screen sieve. The sized granules were then mixed with a lubricating stearic acid. Finally, the granules were compressed into tablets having the target weight and exhibiting a hardness of less than 20 kP. The sustained release tablets contained PPA and varying amounts of phospholipids as shown in TABLE 1. The PPA potency in each of the tablet samples was calculated using a RP-HPLC method.

TABLE 1

| Component | 1:2 PPA:PL90H | 1:1 PPA:PL90H | HPMC |
| --- | --- | --- | --- |
| PPA | 8.25% | 8.25% | 8.25% |
| PHOSPHOLIPON 90H | 16.5% | 8.25% | — |
| HPMC | — | — | 40% |
| Dicalcium Phosphate | 33% | 33% | 44.75% |
| Microcrystalline Cellulose | 24.75% | 24.75% | 6% |
| Liver Blend | 16.5% | 24.75% | — |
| Stearic Acid | 1% | 1% | 1% |
| Total Tablet Weight % | 100% | 100% | 100% |

Figure 1:
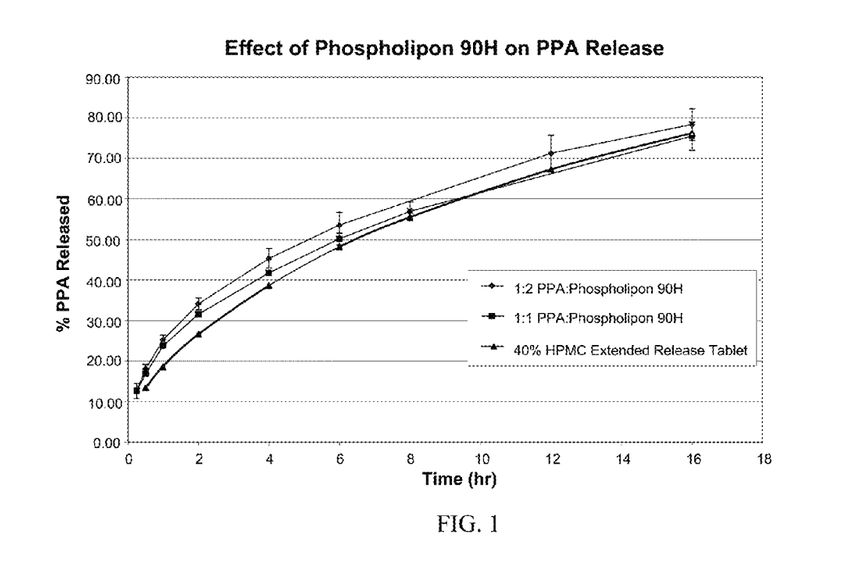
FIG. 1 depicts in vitro dissolution profiles of phenylpropanolamine HCl ("PPA") sustained release tablets at two different phospholipid concentrations as compared to PPA extended release tablets containing hypromellose.

The in vitro dissolution profiles of the sustained release tablets were tested by using a USP Dissolution Apparatus II. Each tested sample was filtered through a 10 micron filter prior to testing. The in vitro dissolution profiles of the sustained release tablets were compared to PPA extended release tablets comprising hypromellose ("HPMC"), 100 mg PPA, and no phospholipids. The formulation of this tablet is shown in TABLE 1. The in vitro dissolution profiles of the sustained release tablets of TABLE 1 are presented in FIG. 1. The tablets containing 16.5% and 8.25% of phospholipids demonstrated similar dissolution rates to the HPMC tablet. Both of these formulations continuously released PPA over a period of 16 hours, thus meeting USP criteria for PPA extended release tablets.

Example 2

This example focused on the effects that PHOSPHOLIPON 20 had on the in vitro dissolution of the chewable sustained release tablets. Sustained release tablets were prepared using the method outlined in Example 1. The sustained release tablets contained 100 mg of PPA and varying amounts of phospholipids (PHOSPHOLIPON 20, "PL20") as shown in TABLE 2. The PPA potency of the tablets was confirmed using the method outlined in Example 1.

TABLE 2

| Component | 1:1 PPA: Phospholipon 20 | 1:2 PPA: Phospholipon 20 | 1:3 PPA: Phospholipon 20 |
| --- | --- | --- | --- |
| PPA | 8.25% | 8.25% | 8.25% |
| PHOSPHOLIPON 20 | 8.25% | 16.5% | 24.75% |
| Dicalcium Phosphate | 30% | 30% | 30% |
| Microcrystalline Cellulose | 21.75% | 21.75% | 13.75% |

TABLE 2-continued

| Component | 1:1 PPA: Phospholipon 20 | 1:2 PPA: Phospholipon 20 | 1:3 PPA: Phospholipon 20 |
| --- | --- | --- | --- |
| Liver Blend | 22% | 22% | 22% |
| Stearic Acid | 1% | 1% | 1% |
| Total Tablet Weight % | 100% | 100% | 100% |

Figure 2:
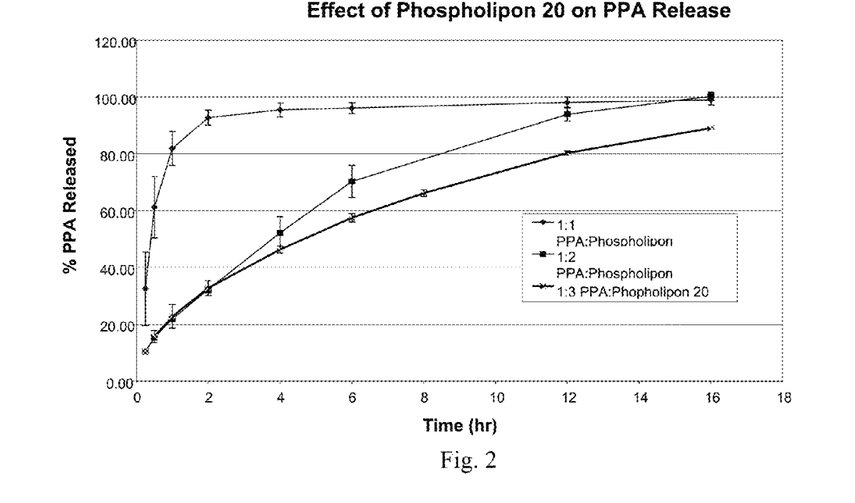
FIG. 2. depicts in vitro dissolution profiles of PPA sustained release tablets at two different phospholipid concentrations.

The in vitro dissolution profiles of the sustained release tablets were tested as outlined in Example 1. The in vitro dissolution profiles of the sustained release tablets in TABLE 2 are presented in FIG. 2. The tablets containing 24.75% and 16.5% of PHOSPHOLIPON 20 demonstrated similar dissolution rates to the HPMC PPA tablet of Example 1. Both of these formulations consistently released PPA over a period of 16 hours, thus meeting USP criteria for PPA extended release tablets.

Example 3

This example focused on the effects that different types of lecithin have on the in vitro dissolution of the chewable sustained release tablets. Sustained release tablets were prepared using the method outlined in Example 1. The sustained release tablets contained 100 mg of PPA and lecithin from either BULKFOODS.COM or ULTRALEC as shown in TABLE 3. The PPA potency of the tablets was confirmed using the method outlined in Example 1.

TABLE 3

| Component | 1:2 PPA:LEC | 1:2 PPA:ULTRALEC |
| --- | --- | --- |
| PPA | 8.25% | 8.25% |
| BULKFOODS.COM lecithin | 16.5% | — |
| ULTRATEC lecithin | — | 16.5% |
| Dicalcium Phosphate | 33% | 33% |
| Microcrystalline Cellulose | 16.5% | 16.5% |
| Liver Blend | 24.75% | 24.75% |
| Stearic Acid | 1% | 1% |
| Total Tablet Weight % | 100% | 100% |

Figure 3:
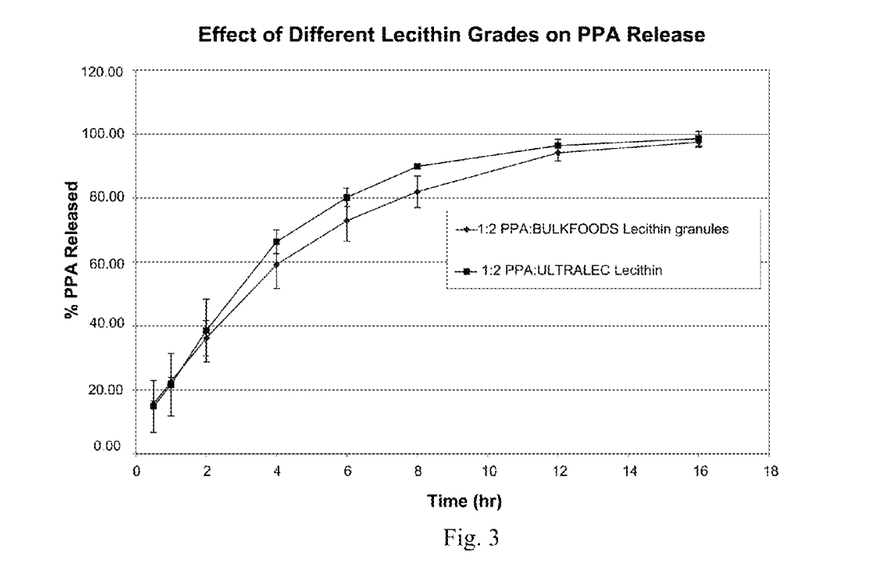
FIG. 3. depicts in vitro dissolution profiles of PPA sustained release tablets formulated with two different types of lecithin.

The in vitro dissolution profiles of the sustained release tablets were tested as outlined in Example 1. The in vitro dissolution profiles of the sustained release tablets in TABLE 3 are presented in FIG. 3. Both sustained release tablets containing lecithin consistently released PPA over a period of 16 hours, thus meeting USP criteria for PPA extended release tablets.

Example 4

This example focused on the production of chewable sustained release tablets containing PPA with taste-masking properties. The sustained release tablets were produced by adding and dissolving PPA in isopropanol at about 30° C. Cholesterol was then added and dissolved in the mixture. Subsequent to dissolving the cholesterol, phospholipids (PHOSPHOLIPON 20) were added to the mixture to thereby produce a homogeneous dispersion. Separately, the dry ingredients (i.e., dicalcium phosphate, microcrystalline cellulose, and liver blend) were added to a low shear mixer and mixed together. The isopropanol mixture was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP. The produced tablets were 1.2 g in weight and round in shape and were suitable for administration to animals for the condition of incontinence. As shown in TABLE 4, the produced tablets contained cholesterol and, in some cases, a mixture of phospholipids. The PPA potency of the tablets was confirmed using the method outlined in Example 1.

TABLE 4

| Component | 1:1 PPA: Cholesterol | 1:1/2:1/2 PPA: Cholesterol/ PL 20 | 1:3/2:3/2 PPA: Cholesterol/ PL 20 |
|---|---|---|---|
| PPA | 8.25% | 8.25% | 8.25% |
| Cholesterol | 8.25% | 4.13% | 5.5% |
| Phospholipon 20 | 0% | 4.13% | 5.5% |
| Dicalcium Phosphate | 33% | 33% | 33% |
| Microcrystalline Cellulose | 24.75% | 24.75% | 23.4% |
| Liver Blend | 25.75% | 25.75% | 24.75% |
| Total Tablet Weight % | 100% | 100% | 100% |

Figure 4:
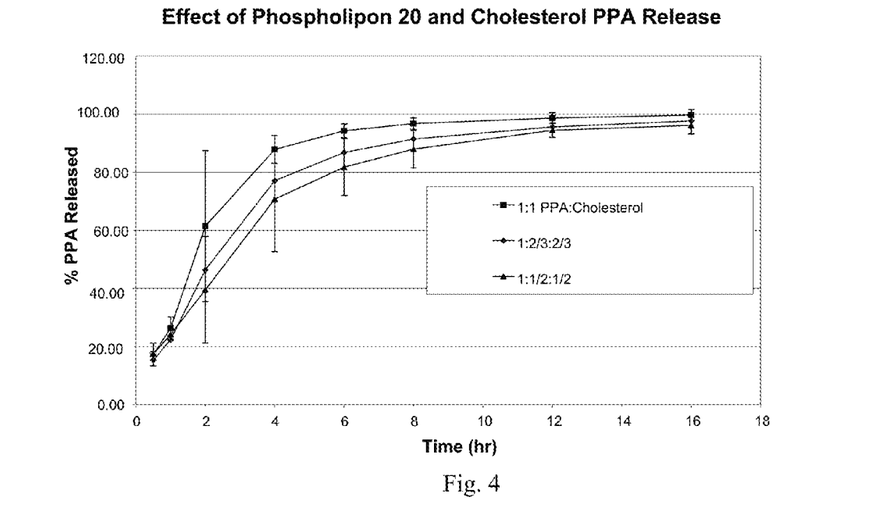
FIG. 4. depicts in vitro dissolution profiles of PPA sustained release tablets formulated with cholesterol and phospholipids.

The in vitro dissolution profiles of the sustained release tablets were tested as outlined in Example 1. As shown in FIG. 4, the combination of cholesterol and phospholipids provided a sustained release of PPA over the course of about 16 hours. In addition, the mixture of cholesterol and phospholipids in the tablets provided an effective taste-masking barrier to the bitter tasting PPA.

Example 5

This example focused on the production of chewable PPA sustained release tablets containing phospholipids and ethylcellulose. The sustained release tablets were produced by adding and dissolving PPA in ethanol at 30° C. Ethylcellulose and phospholipids (PHOSPHOLIPON 90H) were then added to the PPA/ethanol solution and mixed in until a homogenous liquid was obtained without any visible solid particles. Separately, the dry ingredients (i.e., dicalcium phosphate, microcrystalline cellulose, and roast beef flavor) were added to a low shear mixer and mixed together. The ethanol-based homogenous liquid was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets with a 1.6 cm circular biconvex punch/die. As shown in TABLE 5, the produced tablets contained ethylcellulose and phospholipids as the sustained release agents. The PPA potency of the tablets was confirmed using the method outlined in Example 1.

TABLE 5

| Component | 1% Ethylcellulose | 3% Ethylcellulose |
|---|---|---|
| PPA | 8.25% | 8.25% |
| PHOSPHOLIPON 90H | 5.5% | 5.5% |
| Ethylcellulose | 1% | 3% |
| Dicalcium Phosphate | 50% | 50% |
| Microcrystalline Cellulose | 30.2% | 28.2% |
| Roast Beef Flavor | 5% | 5% |
| Total Tablet Weight % | 100% | 100% |

Figure 5:
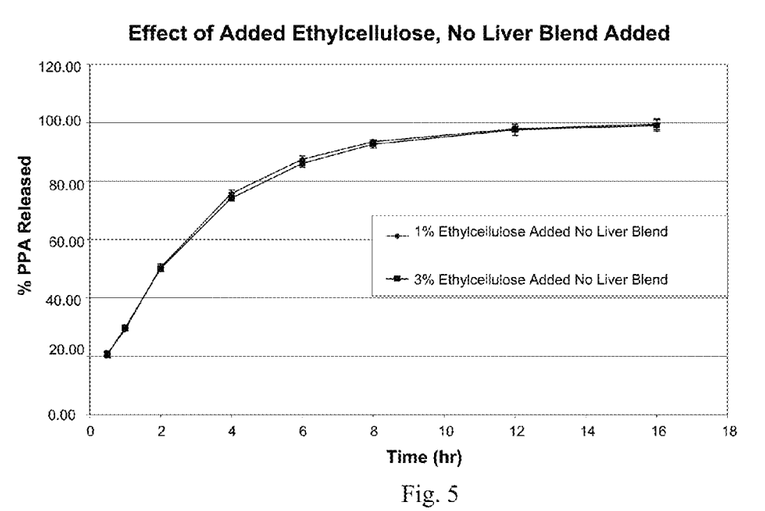
FIG. 5. depicts in vitro dissolution profiles of PPA sustained release tablets formulated with about 1% and 3% ethylcellulose plasticized with phospholipids.

The in vitro dissolution profiles of the sustained release tablets were tested as outlined in Example 1. As depicted in FIG. 5, the combination of ethylcellulose and phospholipids provide a sustained release of PPA over the course of about 16 hours. Furthermore, these results indicate that phospholipids are a good plasticizer for ethylcellulose films, which are used to encapsulate the PPA. Consequently, the ethylcellulose is able to form a continuous and flexible controlled release barrier for the PPA during dissolution. Additionally, the ethylcellulose plasticized with phospholipids showed flexibility that is equivalent to ethylcellulose films cast with traditional plasticizers such as triethyl citrate and dibutyl phthalate.

Example 6

This example focused on the production of chewable PPA sustained release tablets containing glyceryl behenate. The sustained release tablets were produced by adding and dissolving PPA in ethanol at 30° C. Glyceryl behenate (COMPRITOL 888 ATO) was added and mixed into the PPA/ethanol solution. After mixing in the glyceryl behenate, phospholipids (PHOSPHOLIPON 90) were then added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP. As shown in TABLE 6, the produced tablets contained varying amounts of glyceryl behenate. The PPA potency of the tablets was confirmed using the method outlined in Example 1.

TABLE 6

| Component | 5% Glyceryl Behenate | 10% Glyceryl Behenate |
|---|---|---|
| PPA | 8.25% | 8.25% |
| PHOSPHOLIPON 90H | 5.5% | 5.5% |
| Dicalcium Phosphate | 50% | 50% |
| Microcrystalline Cellulose | 25.2% | 20.2% |
| Roast Beef Type Flavor | 5% | 5% |
| Stearic Acid | 1% | 1% |
| Compritol 888 ATO | 5% | 10% |
| Total Tablet Weight % | 100% | 100% |

Figure 6:
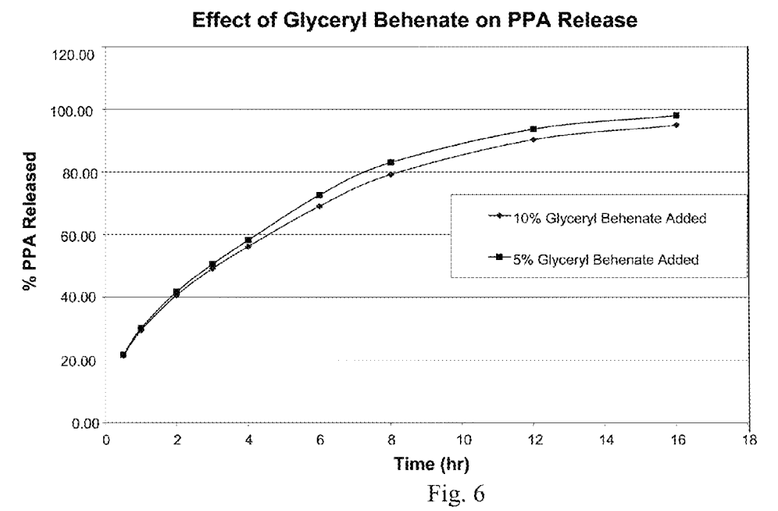
FIG. 6. depicts in vitro dissolution profiles of PPA sustained release tablets formulated with phospholipids and 5% and 10% glyceryl behenate.

The produced tablets were broken into four parts and then subjected to in vitro dissolution analysis as outlined in Example 1. As depicted in FIG. 6, the tablets containing glyceryl behenate consistently released PPA over a period of 16 hours, thus meeting USP criteria for PPA extended release tablets.

Example 7

This example focused on the production of chewable PPA sustained release tablets containing hydrogenated cottonseed oil. The sustained release tablets were produced by adding and dissolving PPA in ethanol at 30° C. Hydrogenated cottonseed oil (STEROTEX NF) was added and mixed into the PPA/ethanol solution. After mixing in the hydrogenated cottonseed oil, phospholipids (PHOSPHOLIPON 90) were then added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogeneous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP. As shown in TABLE 7, the produced tablets contained varying amounts of hydrogenated cottonseed oil. The PPA potency of the tablets was confirmed using the method outlined in Example 1.

TABLE 7

| Component | 10% Sterotex Granulation | 20% Sterotex Granulation |
|---|---|---|
| PPA | 8.25% | 8.25% |
| Phospholipon 20 | 16.5% | 16.5% |
| Dicalcium Phosphate | 40% | 35% |
| Microcrystalline Cellulose | 19.2% | 14.2% |
| Roast Beef Type Flavor | 5% | 5% |
| STEROTEX NF | 10% | 20% |
| Stearic Acid | 1% | 1% |
| Total Tablet Weight % | 100% | 100% |

Figure 7:
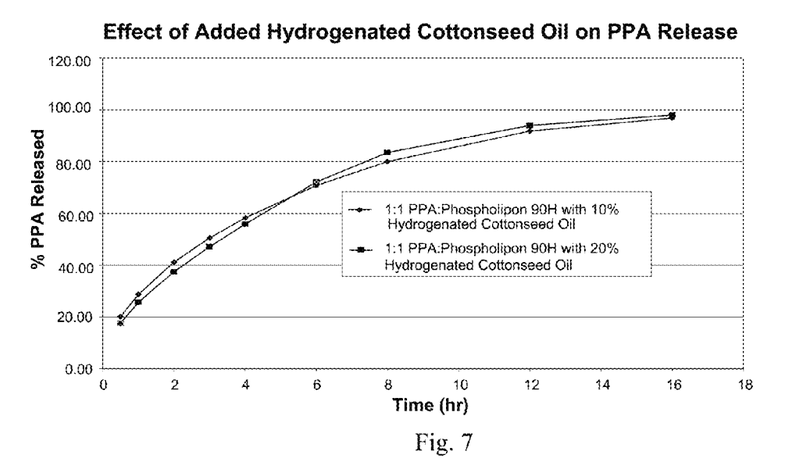
FIG. 7. depicts in vitro dissolution profiles of PPA sustained release tablets formulated with phospholipids and 10% and 20% hydrogenated cottonseed oil.

The produced tablets were broken into four parts and then subjected to in vitro dissolution analysis as outlined in Example 1. As depicted in FIG. 7, the tablets containing hydrogenated cottonseed oil consistently released PPA over a period of 16 hours, thus meeting USP criteria for PPA extended release tablets.

Example 8

This example focused on the production of chewable sustained release tablets containing guaifenesin. The sustained release tablets were produced by adding and dissolving guaifenesin in ethanol at 30° C. Phospholipids (PHOSPHOLIPON 90) were added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP.

TABLE 8

| Component | Guaifenesin Tablet |
|---|---|
| Guaifenesin | 8.25% |
| PHOSPHOLIPON 90H | 8.25% |
| Dicalcium Phosphate | 33% |
| Microcrystalline Cellulose | 24.75% |
| Liver Blend | 24.75% |
| Stearic Acid | 1% |
| Total Tablet Weight % | 100% |

Figure 8:
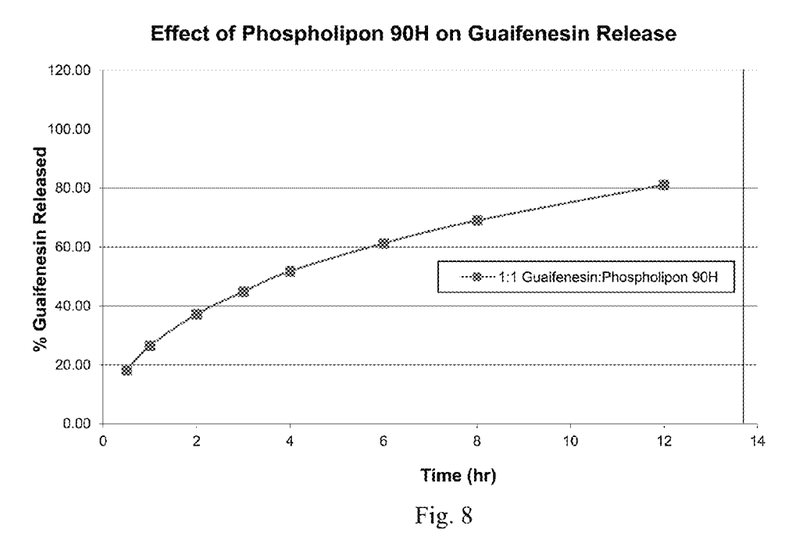
FIG. 8. depicts in vitro dissolution profiles of guaifenesin sustained release tablets formulated with phospholipids.

The produced tablets formed with guaifenesin contained the formulation as depicted in TABLE 8. The guaifenesin potency of the tablets was confirmed using the method outlined in Example 1. The produced tablets were broken into four parts and then subjected to in vitro dissolution analysis as outlined in Example 1. As shown in FIG. 8, the tablets consistently released guaifenesin over a period of 12 hours, thus meeting USP criteria for guaifenesin extended release tablets.

Example 9

This example focused on the production of sustained release tablets containing dextromethorphan. The sustained release tablets were produced by adding and dissolving dextromethorphan in ethanol at 30° C. Phospholipids (PHOSPHOLIPON 90) were added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP.

TABLE 9

| Component | Dextromethorphan Tablet |
|---|---|
| Dextromethorphan HBr | 0.83% |
| PHOSPHOLIPON 90H | 8.25% |
| Dicalcium Phosphate | 40% |
| Microcrystalline Cellulose | 24.75% |
| Liver Blend | 24.75% |
| Stearic Acid | 1% |
| Total Tablet Weight % | 100% |

Figure 9:
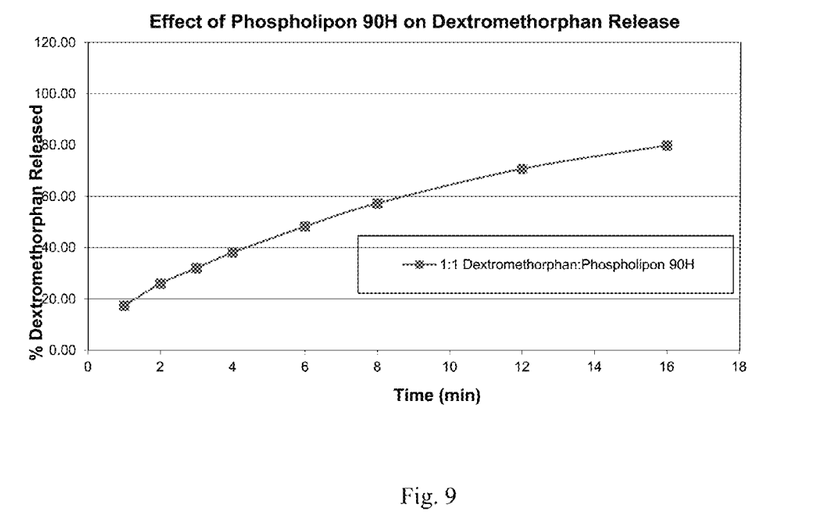
FIG. 9. depicts in vitro dissolution profiles of dextromethorphan HBr sustained release tablets formulated with phospholipids.

The produced tablets formed with dextromethorphan contained the formulation as depicted in TABLE 9. The produced tablets were broken into four parts and then subjected to in vitro dissolution analysis as outlined in Example 1. As shown in FIG. 9, the tablets consistently released dextromethorphan over a period of 12 hours, thus meeting USP criteria for dextromethorphan extended release tablets.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

We claim:

1. A method for preparing tablets of a sustained release composition comprising:
   (a) dissolving or dispersing one or more active ingredients and one or more lipids in a solvent to produce an active-containing solution or suspension, wherein said solvent is present in a sufficient amount to form said solution or said suspension;
   (b) mixing said active-containing solution or suspension with at least one spheronizing or bulking agent to produce a mixture; and
   (c) forming said mixture into tablets comprising a matrix that comprises said lipids and said spheronizing or bulking agent, wherein said active ingredients are encapsulated within said matrix;
   wherein said sustained release composition exhibits an in vitro dissolution rate of said active ingredients as measured by a USP Dissolution Apparatus II of about 10% to 50% after about 2 hours, about 25% to 90% after about 4 hours, more than about 60% after about 12 hours, and more than about 75% after about 16 hours,
   wherein said steps (a)-(c) are performed at temperatures not exceeding the melting point of said one or more lipids,
   wherein said sustained release composition has an in vitro dissolution rate of said active ingredients as measured by a USP Dissolution Apparatus II of no more than 10% during the first 1 to 5 minutes,
   wherein said sustained release composition comprises 0.5 to 15 weight percent of said lipids.

2. The method according to claim 1 further comprising, prior to said step (c), granulating the mixture of step (b) to produce wet granules of said sustained release composition.

3. The method according to claim 2 further comprising, prior to said step (c), drying said wet granules of said sustained release composition to produce dry granules of said sustained release composition.

4. The method according to claim 3 wherein said dry granules contain a residual solvent content of less than 10 weight percent.

5. The method according to claim 3 wherein said step (c) comprises compressing said dry granules of said sustained release composition into said tablets.

6. The method according to claim 1 wherein at least 90% of said one or more active ingredients added to said step (a) remain present in said tablets of step (c).

7. The method according to claim 1 wherein said solvent is selected from the group consisting of methanol, ethanol, n-propanol, isopropanol, t-butanol, ethyl acetate, acetone, and mixtures thereof.

8. The method according to claim 1 wherein said one or more lipids comprise phospholipids, lecithins, ceramides, sphingolipids, steroids, glycolipids, or a combination thereof.

9. The method according to claim 1 wherein said one or more lipids comprise phospholipids, lecithins, or a combination thereof.

10. The method according to claim 1 wherein said at least one bulking or spheronizing agent is selected from the group consisting of microcrystalline cellulose, starch, sodium carboxymethylcellulose, pregelatinized starch, dicalcium phosphate, powdered sugar, calcium phosphate, calcium sulfate, lactose, mannitol, kaolin, sodium chloride, sorbitol, and combinations thereof.

11. The method according to claim 1 wherein said sustained release composition exhibits an in vitro dissolution rate of said active ingredients as measured by a USP Dissolution Apparatus II of at least 20% after about 2 hours.

12. The method according to claim 1 wherein said sustained release composition exhibits an in vitro dissolution rate that is nearly linear for at least 6 hours.

13. The method according to claim 1 wherein the average in vitro dissolution rate of said sustained release composition as measured by a USP Dissolution Apparatus II does not increase by more than about 50% during the first 4 hours after said sustained release composition has been fragmented into a plurality of smaller pieces.

14. The method according to claim 1 wherein said step (a) comprises dissolving said one or more active ingredients and said one or more lipids in said solvent.

15. A method for preparing tablets of a sustained release composition comprising:
   (a) dissolving one or more active ingredients and one or more lipids in a solvent to produce an active-containing solution;
   (b) mixing said active-containing solution with at least one spheronizing or bulking agent to produce a mixture; and
   (c) forming said mixture into tablets comprising a matrix that comprises said lipids and said spheronizing or bulking agent, wherein said active ingredients are encapsulated within said matrix;
   wherein said sustained release composition exhibits an in vitro dissolution rate of said active ingredients as measured by a USP Dissolution Apparatus II of about 10% to 50% after about 2 hours, about 25% to 90% after about 4 hours, more than about 60% after about 12 hours, and more than about 75% after about 16 hours,
   wherein said steps (a)-(c) are performed at temperatures not exceeding the melting point of said one or more lipids,
   wherein said sustained release composition has an in vitro dissolution rate of said active ingredients as measured by a USP Dissolution Apparatus II of no more than 10% during the first 1 to 5 minutes.

16. The method according to claim 15 wherein said solvent is selected from the group consisting of methanol, ethanol, n-propanol, isopropanol, t-butanol, ethyl acetate, acetone, and mixtures thereof.

17. The method according to claim 15 wherein said one or more lipids comprise phospholipids, lecithins, or a combination thereof.

18. The method according to claim 15 wherein said sustained release composition exhibits an in vitro dissolution rate that is nearly linear for at least 6 hours.

19. The method according to claim 15 wherein the average in vitro dissolution rate of said sustained release composition as measured by a USP Dissolution Apparatus II does not increase by more than about 50% during the first 4 hours after said sustained release composition has been fragmented into a plurality of smaller pieces.

20. The method according to claim 1 wherein said sustained release composition has an in vitro dissolution rate of said active ingredients as measured by a USP Dissolution Apparatus II of about 10% to 40% after about 2 hours.

21. The method according to claim 15 wherein said sustained release composition has an in vitro dissolution rate of said active ingredients as measured by a USP Dissolution Apparatus II of about 10% to 40% after about 2 hours.

22. The method according to claim 1 wherein said sustained release composition comprises 6 to 95 weight percent of said active ingredients.

23. The method according to claim 15 wherein said sustained release composition comprises 6 to 95 weight percent of said active ingredients.

24. The method according to claim 15 wherein said sustained release composition comprises 0.5 to 15 weight percent of said lipids.

* * * * *